US009573132B2

(12) United States Patent
Hasson et al.

(10) Patent No.: US 9,573,132 B2
(45) Date of Patent: Feb. 21, 2017

(54) SYSTEM AND METHODS FOR MONITORING THE AMPLIFICATION AND DISSOCIATION BEHAVIOR OF DNA MOLECULES (75) Inventors: Kenton C. Hasson, Gaithersburg, MD (US); Gregory A. Dale, Gaithersburg, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 11/606,006

(22) Filed: Nov. 30, 2006

(65) Prior Publication Data
US 2008/0003593 A1  Jan. 3, 2008

Related U.S. Application Data (60) Provisional application No. 60/806,440, filed on Jun. 30, 2006.

(51) Int. Cl.
*B01L 7/00* (2006.01)
*C12Q 1/68* (2006.01)
*G01N 35/08* (2006.01)
*B01L 3/00* (2006.01)

(52) U.S. Cl.
CPC ............... *B01L 7/52* (2013.01); *C12Q 1/686* (2013.01); *G01N 35/08* (2013.01); *B01L 3/5027* (2013.01); *B01L 2200/143* (2013.01); *B01L 2300/1822* (2013.01); *B01L 2400/0487* (2013.01); *Y10T 436/115831* (2015.01); *Y10T 436/117497* (2015.01)

(58) Field of Classification Search
None
See application file for complete search history.

(56) References Cited

U.S. PATENT DOCUMENTS

| | | |
|---|---|---|
| 6,271,022 B1 | 8/2001 | Bochner |
| 6,689,565 B2 | 2/2004 | Nikiforov |
| 6,699,661 B1 | 3/2004 | Kurane et al. |
| 6,713,264 B2 | 3/2004 | Luttermann et al. |
| 6,960,437 B2 * | 11/2005 | Enzelberger et al. ............ 435/6 |
| 6,979,567 B2 | 12/2005 | Herron et al. |
| 7,081,954 B2 | 7/2006 | Sandstrom |
| 7,090,133 B2 | 8/2006 | Zhu |
| 2001/0036231 A1 | 11/2001 | Easwar et al. |
| 2004/0122559 A1* | 6/2004 | Young et al. ................. 700/269 |
| 2005/0042639 A1 | 2/2005 | Knapp et al. |
| 2005/0117049 A1 | 6/2005 | Suzuki |
| 2005/0135655 A1 | 6/2005 | Kopf-Sill et al. |
| 2005/0189224 A1 | 9/2005 | Parce |
| 2005/0202489 A1 | 9/2005 | Cho et al. |
| 2005/0231723 A1 | 10/2005 | Blasenheim et al. |
| 2005/0266448 A1* | 12/2005 | Hagiwara et al. ................. 435/6 |
| 2006/0000722 A1 | 1/2006 | Parce et al. |
| 2006/0006067 A1 | 1/2006 | Unger |
| 2007/0026421 A1* | 2/2007 | Sundberg et al. ................. 435/6 |

FOREIGN PATENT DOCUMENTS

| | | | |
|---|---|---|---|
| JP | 2003-52391 A | 2/2003 | |
| JP | 2004-305219 A | 11/2004 | |
| JP | 2005-253466 A | 9/2005 | |
| JP | 2005-261354 A | 9/2005 | |
| JP | 2006-511239 A | 4/2006 | |
| JP | 2009-525759 A | 7/2009 | |
| WO | WO9405414 * | 3/1994 | ............. B01F 11/02 |
| WO | 2005/003395 A1 | 1/2005 | |
| WO | 2005075683 A1 | 8/2005 | |

OTHER PUBLICATIONS

Lay et al. (Clinical Chemistry, 1997, 43(12):2262-2267).*
Belgrader et al. (Anal. Chem, 2003, 75, 3446-3450).*
Wang et al. (J Micromech Microeng, 2005, vol. 15, p. 1369-1377).*
Lagally et al., "Single Molecule DNA Amplification and Analysis in an Integrated Microfluidic Device," Anal. Chem., 73:565-570 (2001).
Kopp et al., "Chemical Amplification: Continuous Flow PCR on a Chip," Science, 280:1046-1048 (1998).
Park et al., "Cylindrical Compact Thermal-Cycling Device for Continuous-Flow Polymerase Chain Reaction," Anal. Chem., 75:6029-6033 (2003).
Chunsun Zhang et al., "PCR microfluidic devices for DNA amplification," Biotechnology Advances, Elsevier Publishing, vol. 24, No. 3, pp. 243-284 (2006).
Pavel Neuzil, et al., "Disposable real-time microPCR device: lab-on-a-chip at a low cost," Mol. BioSyst., May 17, 2006, vol. 2, pp. 292-298.
H.P. Lehr, et al., "Real-Time Detection of Nucleic Acid Interactions by Total Internal Reflection Fluorescence," Anal. Chem., May 15, 2003, vol. 75, No. 10, pp. 2414-2420.
Maxim N. Slyadnev, et al., "Temperature measurement inside microchannel and its application to DNA melting analysis on a chip," Abstract of the 3rd Meeting of Chemistry and Micro Systems, 2001, p. 5.
Aman Russom, et al., "Rapid Melting Curve Analysis on Monolayered Beads for High-Throughput Genotyping of Single-Nucleotide Polymorphisms," Anal. Chem., Apr. 1, 2006, vol. 78, pp. 2220-2225.

(Continued)

*Primary Examiner* — Stephanie K Mummert
(74) *Attorney, Agent, or Firm* — Rothwell, Figg, Ernst & Manbeck, P.C.

(57) ABSTRACT

The present invention relates to systems and methods for monitoring the amplification of DNA molecules and the dissociation behavior of the DNA molecules. A method according to one embodiment of the invention may include the steps of: forcing a sample of a solution containing real-time PCR reagents to move though a channel; and while the sample is moving through an analysis region of the channel, performing the steps of: (a) cycling the temperature of the sample until the occurrence of a predetermined event; (b) after performing step (a), causing the sample's temperature to gradually increase from a first temperature to a second temperature; and (c) while the step of gradually increasing the sample's temperature is performed, using an image sensor to monitor emissions from the sample.

25 Claims, 11 Drawing Sheets

(56) References Cited

OTHER PUBLICATIONS

E.B. Khomyakova, et al., "Innovative Instrumentation for Microarray Scanning and Analysis: Application for Characterization of Oligonucleotide Duplexes Behavior," Cellular and Molecular Biology, 2004 vol. 50, No. 3, pp. 217-224.

\* cited by examiner

SYSTEM AND METHODS FOR MONITORING THE AMPLIFICATION AND DISSOCIATION BEHAVIOR OF DNA MOLECULES

CROSS REFERENCE TO RELATED APPLICATION(S)

The present application claims the benefit to U.S. Provisional Patent Application Ser. No. 60/806,440, filed on Jun. 30, 2006, which is incorporated herein by this reference.

BACKGROUND

Field of the Invention

The present invention relates to systems and methods for monitoring the amplification of DNA molecules and the dissociation behavior of the DNA molecules.

Discussion of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. Polymerase chain reaction (PCR) is a well-known technique for amplifying DNA.

With PCR, one can quickly produce millions of copies of DNA starting from a single template DNA molecule. PCR includes a three phase temperature cycle of denaturation of the DNA into single strands, annealing of primers to the denatured strands, and extension of the primers by a thermostable DNA polymerase enzyme. This cycle is repeated a number of times so that at the end of the process there are enough copies to be detected and analyzed. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

In some applications, it is important to monitor the accumulation of DNA products as the amplification process progresses. Real-time PCR refers to a growing set of techniques in which one measures the buildup of amplified DNA products as the reaction progresses, typically once per PCR cycle. Monitoring the amplification process over time allows one to determine the efficiency of the process, as well as estimate the initial concentration of DNA template molecules. For general details concerning real-time PCR see *Real-Time PCR: An Essential Guide*, K. Edwards et al., eds., Horizon Bioscience, Norwich, U.K. (2004).

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Anal Chem* 73:565-570 (2001)), Kopp et al. (*Science* 280:1046-1048 (1998)), Park et al. (*Anal Chem* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Once there are a sufficient number of copies of the original DNA molecule, the DNA can be characterized. One method of characterizing the DNA is to examine the DNA's dissociation behavior as the DNA transitions from double stranded DNA (dsDNA) to single stranded DNA (ssDNA) with increasing temperature. The process of causing DNA to transition from dsDNA to ssDNA is sometimes referred to as a "high-resolution temperature (thermal) melt (HRTm)" process, or simply a "high-resolution melt" process.

Accordingly, what is desired is a system for monitoring the DNA amplification process and for determining the DNA's dissociation behavior.

SUMMARY OF THE INVENTION

The present invention relates to systems and methods for performing and monitoring real-time PCR and HRTm analysis.

In one aspect, the present invention provides a method that includes the steps of: (a) introducing into a microchannel at least one bolus containing nucleic acid; (b) forcing the bolus to move through the microchannel; (c) while the bolus is moving through the microchannel, amplifying nucleic acid contained in the bolus and using an image sensor to determine whether the nucleic acid has been sufficiently amplified; (e) if the nucleic acid has not been sufficiently amplified, then repeating step (c), otherwise, while the bolus is still moving through the microchannel, causing dsDNA within the bolus to transition to ssDNA and using an image sensor to capture images of the bolus. In some embodiments, the step of using the image sensor to capture an image of the bolus comprises determining a region of interest and then reading out only those pixels of the image sensor that are within the region of interest and capturing at least about 5 images of the bolus per second.

In some embodiments, the step of using the image sensor to determine whether the nucleic acid has been sufficiently amplified includes using the image sensor to capture an image of the bolus and processing the captured image data to determine the intensity of light emitted from the bolus. A value representing the determined intensity may be compared to a threshold value to determine whether the nucleic acid has been sufficiently amplified.

In some embodiments, once it has been determined that the nucleic acid has been sufficiently amplified, a process for causing the dsDNA within the bolus to transition to ssDNA is initiated (e.g., if the result of the comparison indicates that the value representing the determined intensity is greater than the threshold value, then the melting process is initiated at least shortly after the determination is made).

In some embodiments, the step of initiating the process comprises configuring a heating system to gradually increase the temperature of the bolus. Preferably, the temperature is increased at or about a constant rate (e.g., a constant rate of between about 0.1 and 1 degree Celsius per second).

In another aspect, the present invention provides a system that includes the following elements: a substrate comprising a microfluidic channel; a thermal generating unit operable to provide heat to and absorb heat from at least a portion of the microfluidic channel; an image sensor disposed in relation to the substrate such that said portion of the channel is within the field of view of the image sensor; and an image processing system coupled to the image sensor and configured to: (i) receive image data from the image sensor and (ii) use image data from the image sensor to determine whether the intensity of emissions from a nucleic acid sample traveling through said portion of the channel equals or exceeds a predetermined emission intensity threshold; and a temperature controller configured to control the thermal generating unit and configured to cause the thermal generating unit to gradually ramp the temperature of the portion of the channel from a first temperature to a second temperature in response to the image processing system determining that the intensity of emissions from a nucleic acid sample traveling through said portion of the channel equals or exceeds a predetermined emission intensity threshold.

In some embodiments, the thermal generating unit is configured to ramp the temperature by steadily increasing the amount of heat provided at a thermal ramp rate of between about 0.1 to 1 degree Celsius (C) per second. The temperature controller may further be configured to cause the thermal generating unit to cycle the temperature of the portion of the channel in response to a predetermined input.

The system may further include an image sensor controller. The image sensor controller may be operable to cause the image sensor to capture images of at least a segment of said portion of the channel that is within the field of view of the image sensor while the thermal generating unit cycles the temperature of the portion of the channel. The image sensor controller may also be operable to cause the image sensor to capture images of at least a segment of said portion of the channel that is within the field of view of the image sensor while the thermal generating unit ramps the temperature of the portion of the channel. In some embodiments, the image sensor controller is operable to cause the image sensor to capture at least 1 image every 90 seconds while the thermal generating unit cycles the temperature and to capture at least 5 images per second while the thermal generating unit ramps the temperature.

The system may also include an excitation source for producing electromagnetic radiation directed at the portion of the channel. In some embodiments, the system may further include a second excitation source for illuminating at least a segment of the portion of the channel in response to the image processing system determining that the intensity of emissions from a nucleic acid sample traveling through said portion of the channel equals or exceeds a predetermined emission intensity threshold.

In another aspect, the present invention provides a method that includes the steps of: (i) forcing a sample of a solution containing real-time PCR reagents to move though a channel; and (ii) while the sample is moving through an analysis region of the channel, performing the steps of: (a) cycling the temperature of the sample until the occurrence of a predetermined event; (b) after performing step (a), causing the sample's temperature to gradually increase from a first temperature to a second temperature; and (c) while the step of gradually increasing the sample's temperature is performed, using an image sensor to monitor emissions from the sample. In some embodiments, the step of gradually increasing the temperature of the sample from the first temperature to the second temperature comprises increasing the temperature at or about a constant rate (e.g., between about 0.1 and 1 degrees Celsius per second).

In some embodiment, the method may further include the step of determining whether the predetermined event has occurred. This step may include determining whether nucleic acid in the sample has been sufficiently amplified by, for example, determining the intensity of light emitted from the sample and comparing the determined intensity to an intensity threshold value. The step of determining the intensity of light emitted from the sample may include the step of using an image sensor to capture an image of the sample and the image capturing step may include determining a region of interest and then reading out only those pixels of the image sensor that are within the region of interest.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of a reference number identifies the drawing in which the reference number first appears.

DETAILED DESCRIPTION OF PREFERRED EMBODIMENTS

Figure 1:
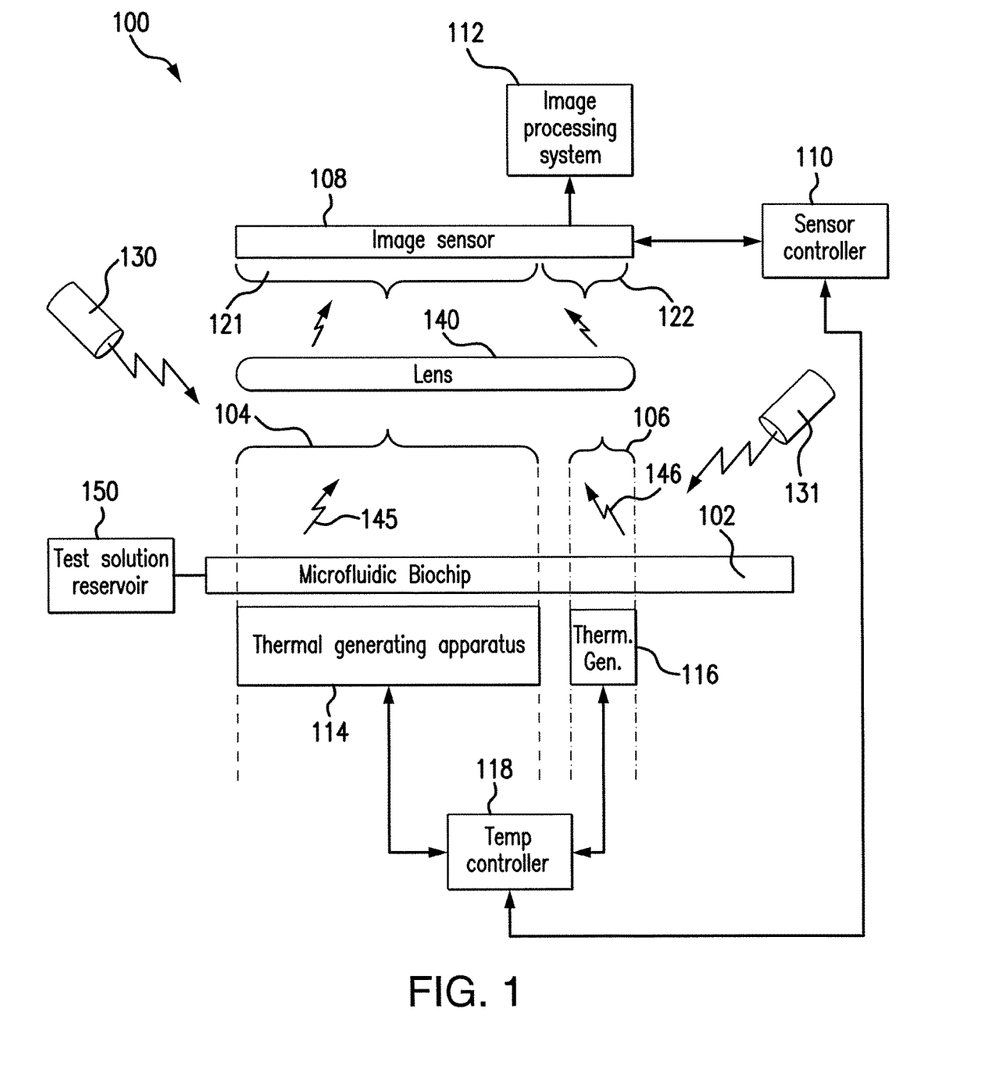
FIG. 1 is a functional block diagram of a genomic analysis system according to one embodiment.

Referring to the drawings, FIG. 1 illustrates a nucleic acid analysis system 100 according to an embodiment. As shown in FIG. 1, system 100 includes a microfluidic biochip 102 having a PCR processing zone 104 (i.e., a zone in which DNA is amplified) and a HRTm analysis zone 106 (i.e., a zone in which the dissociation behavior of the amplified DNA is examined).

Figure 2:
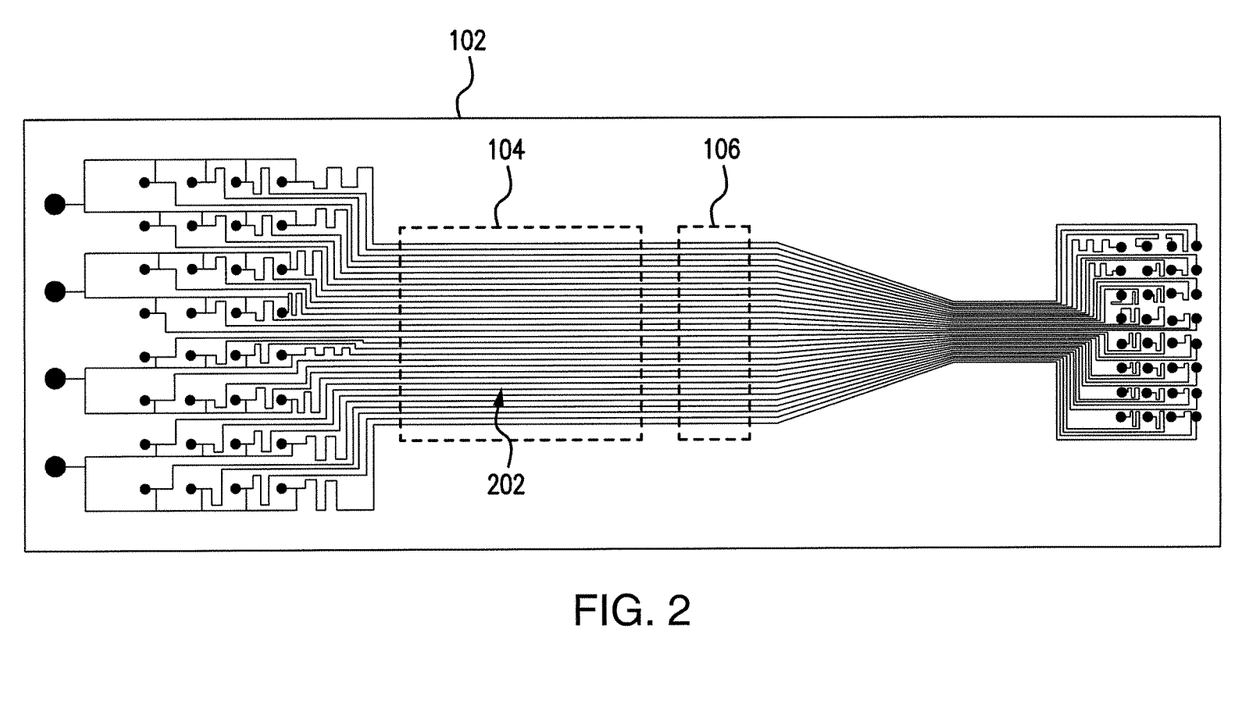
FIG. 2 is a top view of a biochip according to one embodiment.

FIG. 2 is a top view of biochip 102 according to some embodiments. As shown in FIG. 2, biochip 102 includes a number of microcfluidic channels 202. In the example shown, there are 8 microfluidic channels, but it is contemplated that chip 102 may have more or less than 8 channels.

As shown, a first portion of each microfluidic channel may be within the PCR processing zone 104 and a second portion of each microfluidic channel may be within the HRTm analysis zone 106. As further shown in FIG. 1, zone 106 may immediately follow zone 104 and the length of zone 104 may be significantly greater than the length of zone 106 (e.g., the length of zone 104 may be 5 times the length of zone 106).

Although FIG. 1 shows that there is a small gap between zones 104 and 106, it is contemplated that there no gap exists between the zones (i.e., it is contemplated that zone 106 not only immediately follows zone 104, but also shares a common boundary with zone 104). In some embodiments, when system 100 is in use, at least one channel 202 receives a sample (or "bolus") of a solution containing real-time PCR reagents. A force may be used to cause the bolus to travel through the channel such that the bolus traverses PCR zone 104 prior to entering HRTm zone 106. One system and method for performing PCR in a microfluidic device is disclosed in U.S. patent application Ser. No. 11/505,358, filed on Aug. 17, 2006, incorporated herein by reference.

Referring back to FIG. 1, genomic analysis system 100 further includes an image sensor 108, a controller 110 for controlling image sensor 108, and an image processing system 112 for processing the image data produced by image sensor 108. Image sensor 108 may be implemented using a CMOS image sensor, a CCD image sensor, or other image sensor. For example, in one embodiment, sensor 108 is a CMOS sensor with an effective 12.7 mega pixel resolution and having a size of 36×24 mm, which is available from Canon Inc.

Image sensor 108 has a first image sensor region 121 and a second image sensor region 122. Image sensor region 121 has a different field of view than image sensor region 122. In preferred embodiments, image sensor 108 is positioned with respect to chip 102 such that at least a portion of PCR processing zone 104 is within the field of view of sensor region 121 and at least a portion of HRTm zone 106 is within the field of view of sensor region 122.

Figure 3:
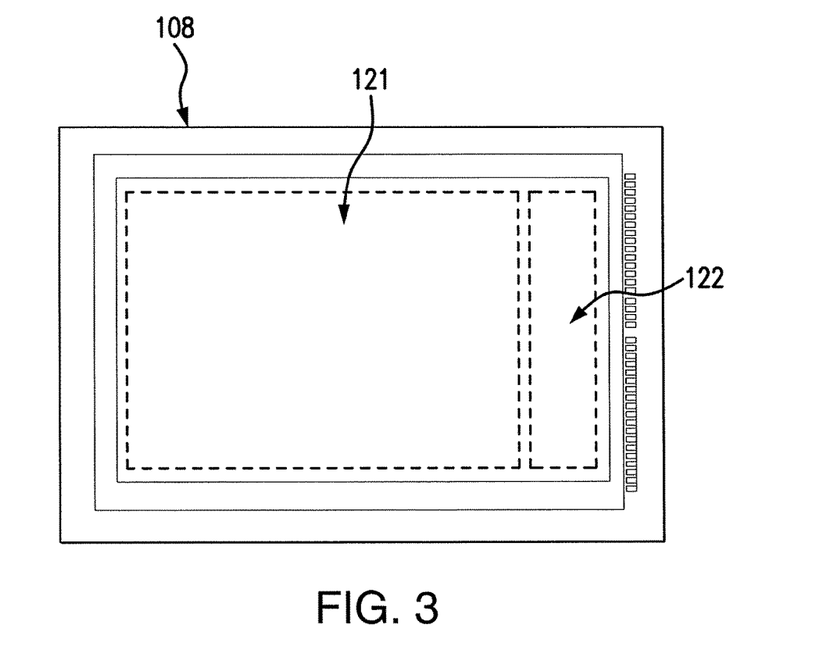
FIG. 3 is a view of an image sensor according to one embodiment.

Referring now to FIG. 3, FIG. 3 is a view of the light sensitive surface of image sensor 108. This view better illustrates the two image sensor regions 121, 122. As shown, the area of image sensor region 122 may be significantly smaller than the area of image sensor region 121 (e.g., ⅕ the area or less). In some embodiments the widths of the two regions 121, 122 are the same, but the lengths are different.

Figure 8:
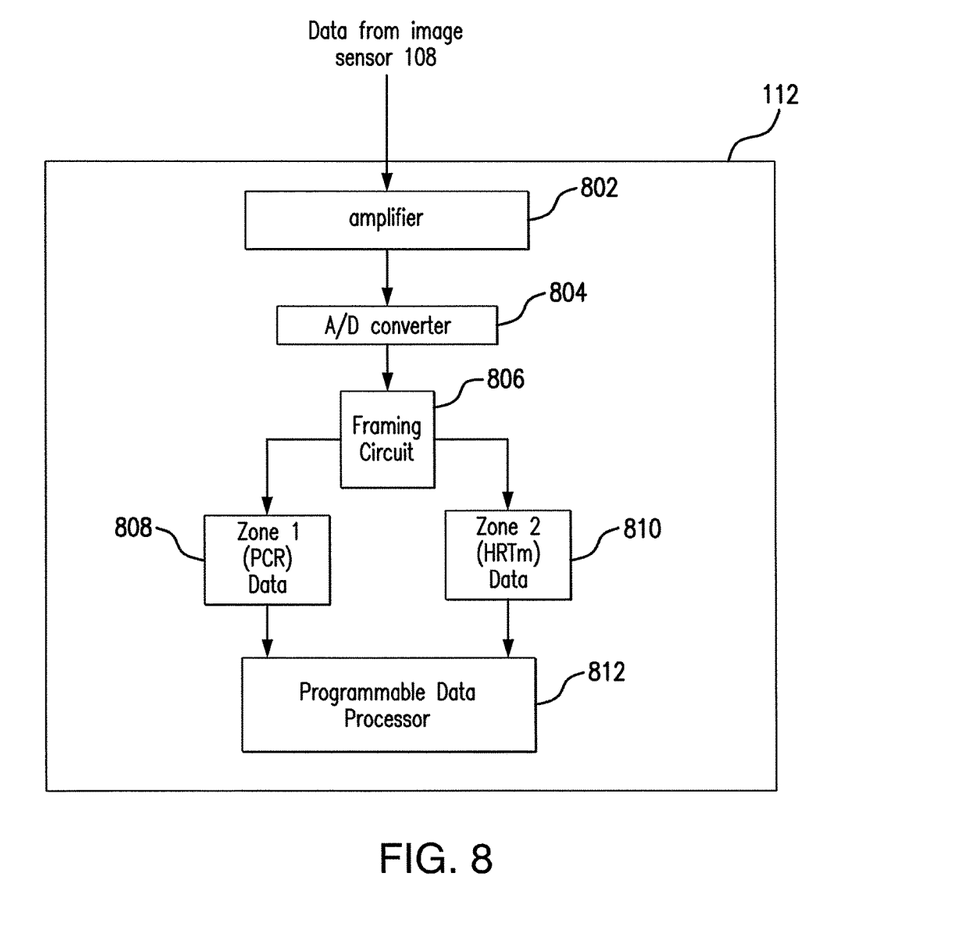
FIG. 8 is a functional block diagram illustrating an embodiment of image processing system.

Referring now to FIG. 8, FIG. 8 is a functional block diagram illustrating an embodiment of image processing system 112. As shown in FIG. 8, system 112 receives data output from image sensor 108. System 112 may include an amplifier 802 to amplify the data from image sensor 108. In one non-limiting embodiment, amplifier 802 may amplify the data for greater than 3200 ISO sensitivity. The amplified data may be converted to a digital signal by, for example, a 16 bit analog-to-digital (A/D) converter 804. In one embodiment, utilization of a 16 bit A/D converter provides a high level of dynamic range and low end bit resolution. The digital signal output from A/D converter 804 may be processed by a framing circuit 806, which may be configured to store data produced from image sensor region 121 in a zone 1 data buffer 808 and store data produced from image sensor region 122 in a zone 2 data buffer 810. A programmable data processor 812 may be programmed to process data in buffers 810 and 812 to, among other things, determine and record the intensity of the fluorescence from zones 104 and 106.

By configuring image sensor 108 and chip 102 as described above, a single image sensor is able to (i) produce data corresponding to the intensity of emissions from PCR zone 104 and (ii) produce data corresponding to the intensity of emissions from HRTm zone 106. Thus, while utilizing only a single image sensor, system 100 can simultaneously monitor (1) the amplification of a sample of DNA and (2) the dissociation behavior of a different DNA sample.

As further illustrated in FIG. 1, system 100 may include one or more thermal generating apparatuses. In the embodiment shown, system 100 includes a first thermal generating apparatus 114 and a second thermal generating apparatus 116 and a controller 118 for controlling apparatuses 114, 116. In one embodiment, first thermal generating apparatus creates a first thermal zone in PCR processing zone 104 and second thermal generating apparatus creates a second thermal zone in the HRTm analysis zone 106.

Each thermal generating apparatus 114, 116 is configured to provide heat to and/or absorb heat from chip 102, and, thus, may include one or more heat sources and/or heat sinks (e.g., each thermal generating apparatus 114, 116 may include a peltier device or other heat source or sink). More specifically, in the embodiment shown, thermal apparatus 114 is configured to provide heat to and/or absorb heat from PCR zone 104, and thermal apparatus 116 is configured to provide heat to and/or absorb heat from HRTm zone 106.

While only one temperature controller is shown, it is contemplated that each thermal generating apparatus may have its own controller. Additionally, although system 100 may have a single temperature controller, the thermal generating apparatuses may be operated independently so apparatus 116 can be used to perform HRTm analysis in zone 106 while at the same time apparatus 114 is used to cause PCR to occur in zone 104.

That is, in some embodiments, the first thermal generating apparatus 114 is configured such that while a bolus is within zone 104, thermal generating apparatus 114 cycles the temperature in zone 104 to achieve PCR, and thermal generating apparatus 116 is configured such that, when a bolus enters zone 106, thermal generating apparatus 116 provides a substantially steadily increasing amount of heat to zone 106 to cause the bolus to undergo HRTm analysis (i.e., to cause the dsDNA in the bolus to transition to ssDNA). In one example, thermal generating apparatus 116 may provide a thermal ramp rate of typically 0.1 to 2 degree Celsius (C) per second, with the preferred ramp rate being between 0.5 and 1 degree Celsius (C) per second.

Referring now to sensor controller 110, sensor controller 110 may be configured so that, for each bolus that undergoes HTRm analysis in the HRTm analysis zone, image sensor controller 110 causes sensor 108 to capture preferably at least about 10 images per second from image sensor region 122 for at least about 1 minute while the bolus undergoes the HRTm analysis (typically it captures the images for an uninterrupted duration of about 5 minutes). In embodiments where the ramp rate is faster, the image sensor controller 110 may cause sensor 108 to capture the images at a rate of about 20 images per second. In many embodiments, the goal is to achieve a temperature resolution of 0.1 degree Celsius or better.

In some embodiments, to achieve the high 10 images/second frame rate, the sensor may be implemented using a CMOS sensor and the controller may be configured to window the CMOS sensor to read out only the pixels of interest (e.g., some or all of the pixels within image sensor region 122).

In some embodiments, system 100 may further include an excitation source 130 (e.g., a laser or other excitation source) for illuminating zones 104 and/or 106. Additional excitation sources (e.g., source 131) may also be employed. System 100 may further include a lens 140 that is disposed between chip 102 and image sensor 108. In such embodiments, lens 140 may be configured to focus onto the first image sensor region 121 light 145 coming from the PCR processing zone 104 and to focus onto the second image sensor region 122 light 146 coming from the HRTm analysis zone 106.

Figure 4:
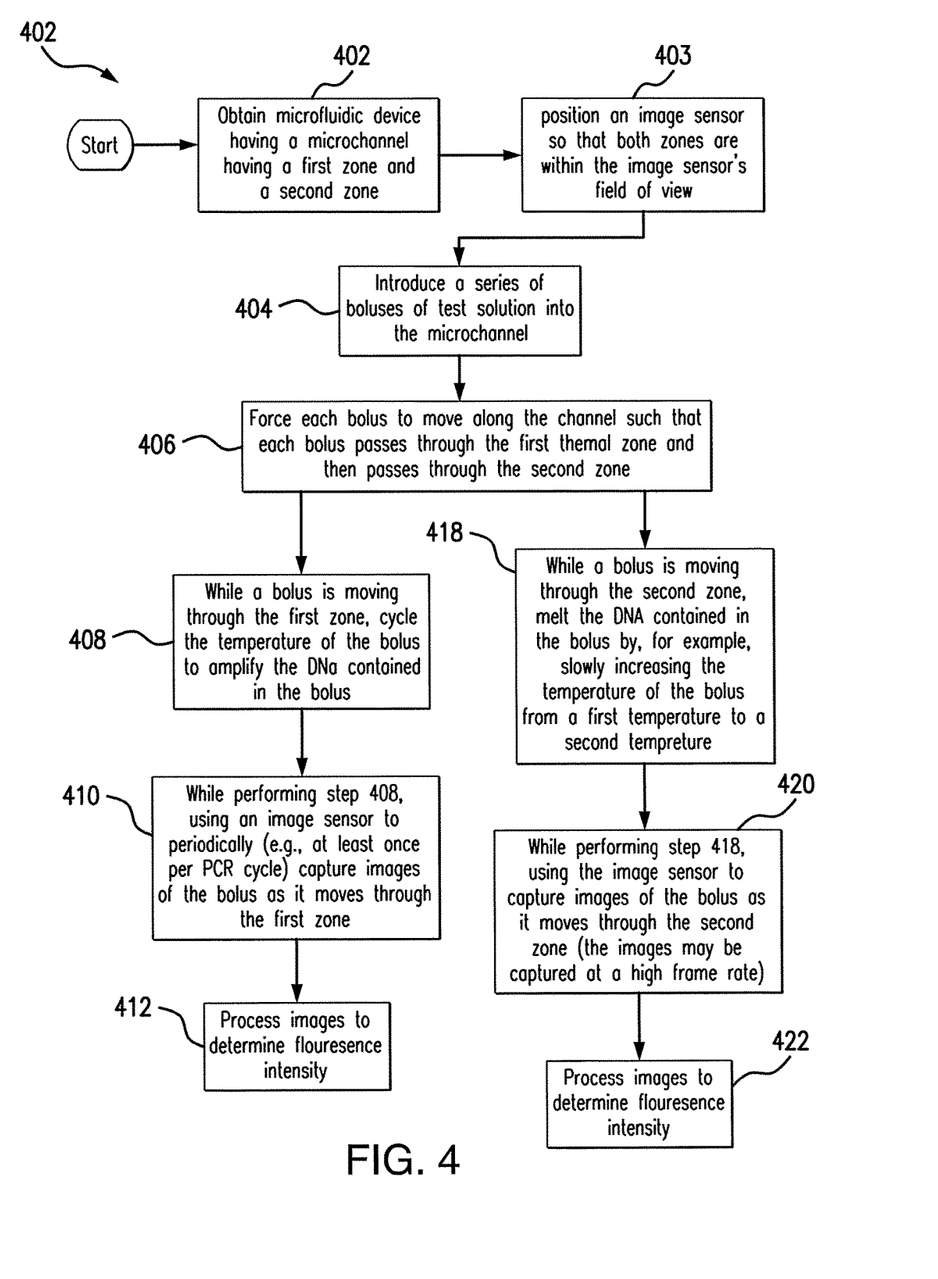
FIG. 4 is a flow chart illustrating a process according to one embodiment.
Figure 5:
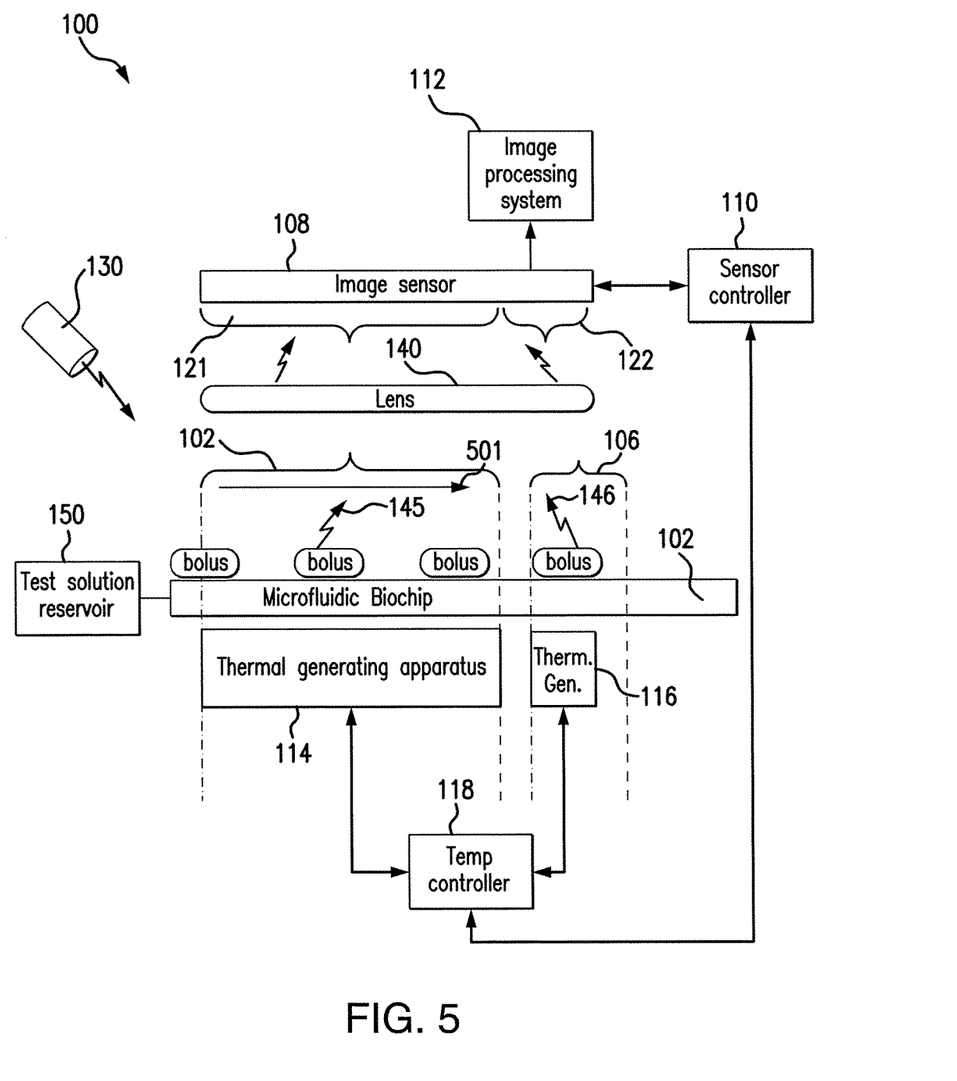
FIG. 5 is functional block diagram of a genomic analysis system according to one embodiment.

Referring now to FIG. 4, FIG. 4 is a flow chart illustrating a process 400 according to an embodiment. Process 400 may begin in step 402, where a microfluidic device 102 having a mircochannel having a PCR processing zone 104 (the first thermal zone) and a HRTm analysis zone 106 (the second thermal zone) is obtained (see FIG. 5). In step 403, an image sensor (e.g., image sensor 108) is obtained and positioned such that both the first and second thermal zones are simultaneously within the image sensor's field of view.

In step 404, a series of boluses of a test solution are introduced into the microchannel (the test solution may be stored in a test solution reservoir 150 (see FIG. 1)). In step 406, each bolus is forced to move along the channel such that each bolus passes through the PCR processing zone and then enter and moves through the HRTm analysis zone. This step is pictorially illustrated in FIG. 5. Arrow 501 shows the direction in which the series of boluses move. In some embodiments, the boluses continuously move at a constant speed.

Figure 6:
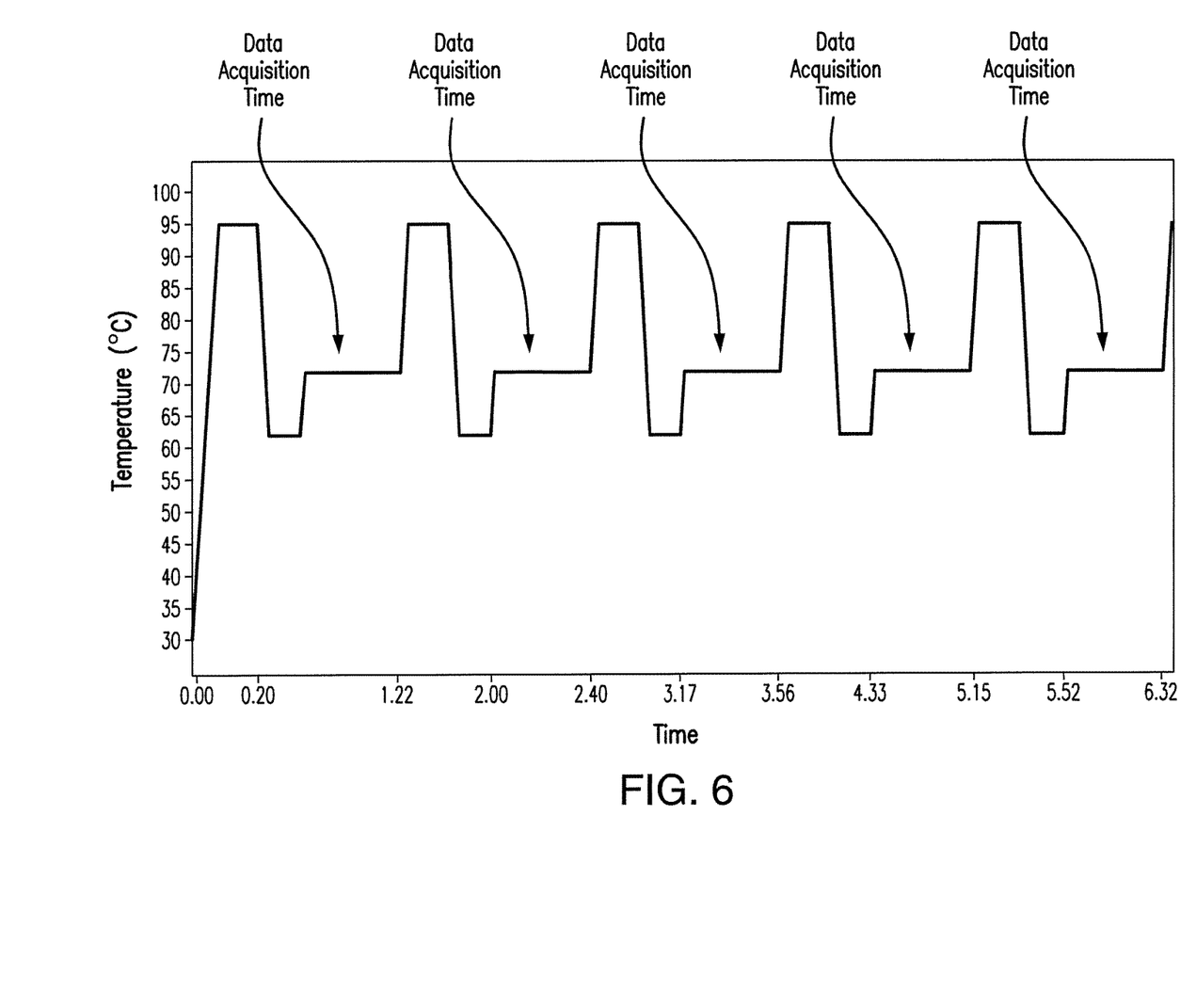
FIG. 6 illustrates a first temperature profile according to one embodiment.

In step 408, while one or more boluses are moving through the PCR processing zone, the temperature of the PCR processing zone is cycled to amplify the DNA in each bolus. FIG. 6 illustrates the temperature profile of the PCR processing zone, according to some embodiments, as a result of step 408 being performed. As shown in FIG. 6, and as is well known in the art, one temperature cycle consists of: (1) holding the temperature of the PCR processing zone at a first temperature (t1) (e.g., 52 degrees C.) for a first period of time (p1) (e.g., 5 seconds), (2) then rapidly increasing the temperature from t1 to t2 (e.g., 72 degrees C.) and holding the temperature at t2 for a second period of time (p2) (e.g., 10 seconds), (3) then rapidly increasing the temperature from t2 to t3 (e.g., 94 degrees C.) and holding the temperature at t3 for a third period of time (p3) (e.g., 5 seconds), and (4) then rapidly dropping the temperature back to t1 so that the cycle may repeat. The above described temperature cycle may be referred to as a "PCR cycle." In some embodiments, the PCR cycles repeat for period of time (e.g., as long as necessary to produce a sufficient amount of DNA—typically about 20-40 PCR cycles).

In step 410, image sensor 108 is used to capture images of at least one bolus within the PCR processing zone as the bolus moves through the zone and as the temperature of the zone is cycled as described above. In some embodiments, the images are captured only during the "middle" of the PCR cycle (i.e., the time during which the temperature is held at t2), as shown in FIG. 6. In some embodiments, sensor controller 110 controls the image capturing and windows images sensor 108 so that the step of capturing an image of the bolus includes reading only the pixels of the image sensor 108 that are within image sensor region 121, or a subset of those pixels, such as, for example, the pixels that receive light from the bolus and one or more immediately surrounding pixels.

In step 412, the images captured in step 410 are processed by, for example, image processing system 112. Image processing system 412 may include one or more processors programmed by software to determine the intensity of fluorescence emitted from the bolus as a function of time.

Figure 7:
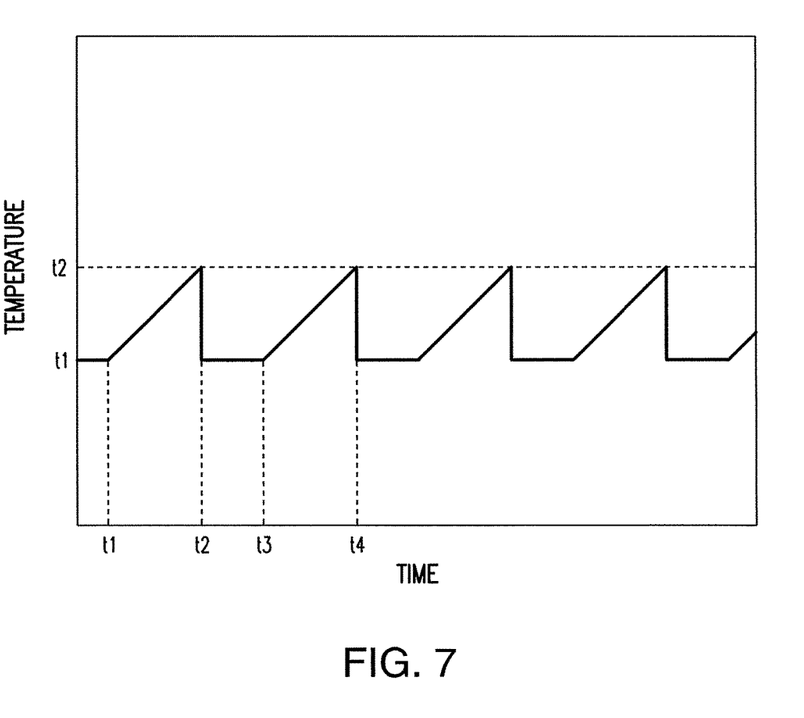
FIG. 7 illustrates a second temperature profile according to one embodiment.

In step 418, when (or shortly after) a bolus enters the HRTm analysis zone and while it moves though the zone, the temperature of the HRTm analysis zone is increased to cause dsDNA within the bolus to transition to ssDNA. FIG. 7 illustrates the temperature profile of the HRTm analysis zone, according to some embodiments. In the example shown in FIG. 7, a first bolus enters the HRTm analysis zone at (or shortly after) time t1 and remains within the zone until (or shortly after) time t2 and a second bolus enters the HRTm analysis zone at (or shortly after) time t3 and remains within the zone until (or shortly after) time t4. As shown in FIG. 7, while the first and second samples are within the HRTm analysis zone, the temperature of the zone may increase, at a substantially constant rate (e.g., 0.1 to 1 degrees C. per second), from temperature t1 (e.g., about 65 degrees C.) to temperature t2 (e.g., about 95 degrees C.), which temperature increase should cause dsDNA within the samples to transition to ssDNA.

In one embodiment, amplification by PCR is performed in the presence of a dsDNA binding fluorescent dye. The dye does not interact with ssDNA but actively binds with dsDNA and fluoresces brightly in this state. This shift in fluorescence can be used firstly to measure the increase in DNA concentration in the PCR processing zone and then to directly measure thermally-induced DNA dissociation by HRTm. Initially, fluorescence is high in a melt analysis because the sample starts as dsDNA, but fluorescence diminishes as the temperature is raised and DNA dissociates into single strands. The observed "melting" behavior is characteristic of a particular DNA sample. A melt curve is typically made and plots the transition from high fluorescence of the initial pre-melt phase through the sharp fluorescence decrease of the melt phase to basal fluorescence at the post-melt phase. Fluorescence decreases as DNA binding dye is released from double-stranded DNA as it dissociates (melts) into single strands. The midpoint of the melt phase, at which the rate of change in fluorescence is greatest, defines the temperature of melting (TM) of the particular DNA fragment under analysis.

Suitable dsDNA binding dyes included SYBR® Green 1 (Invitrogen Corp., Carlsbad, Calif.), SYTO® 9 (Invitrogen Corp., Carlsbad, Calif.), LC Green® (Idaho Technologies, Salt Lake City, Utah) and Eva Green™ (Biotium Inc, Hayward, Calif.). Of these dyes, SYTO® 9, LC Green® and Eva Green™ have low toxicity in an amplification reaction and can therefore be used at higher concentrations for greater saturation of the dsDNA sample. Greater dye saturation means measured fluorescent signals have higher fidelity, apparently because there is less dynamic dye redistribution to non-denatured regions of the nucleic strand during melting and because dyes do not favor higher melting temperature products (Wittwer et al., *Clinical Chemistry* 49:853-860 (2003)). The combination of these characteristics provides greater melt sensitivity and higher resolution melt profiles.

In step 420, image sensor 108 is used to capture images of the bolus within the HRTm analysis zone as the bolus moves through the zone and while the temperature of the zone is increased as described above. In some embodiments, when the image sensor is used to capture images of the bolus within the HRTm analysis zone the image sensor is in the same position and orientation it was in when it was used in step 410 to capture images of the bolus within the PCR processing zone.

In some embodiments, in step 420, the images are captured at a high frame rate (e.g., more than 5 images per second and preferably at least about 10 images per second).

In some embodiments, sensor controller 110 controls the image capturing and windows images sensor 108 so that the step of capturing an image of the bolus includes reading only the pixels of the image sensor 108 that are within image sensor region 122, or a subset of those pixels, such as, for example, the pixels that receive light from the bolus and one or more immediately surrounding pixels.

In step 422, the images captured in step 420 are processed by, for example, image processing system 112. Image processing system 412 may include one or more processors programmed by software to determine the intensity of fluorescence emitted from the bolus as a function of time.

As illustrated in FIG. 4, steps 418-420 may occur simultaneously with steps 408-410.

Figure 9:
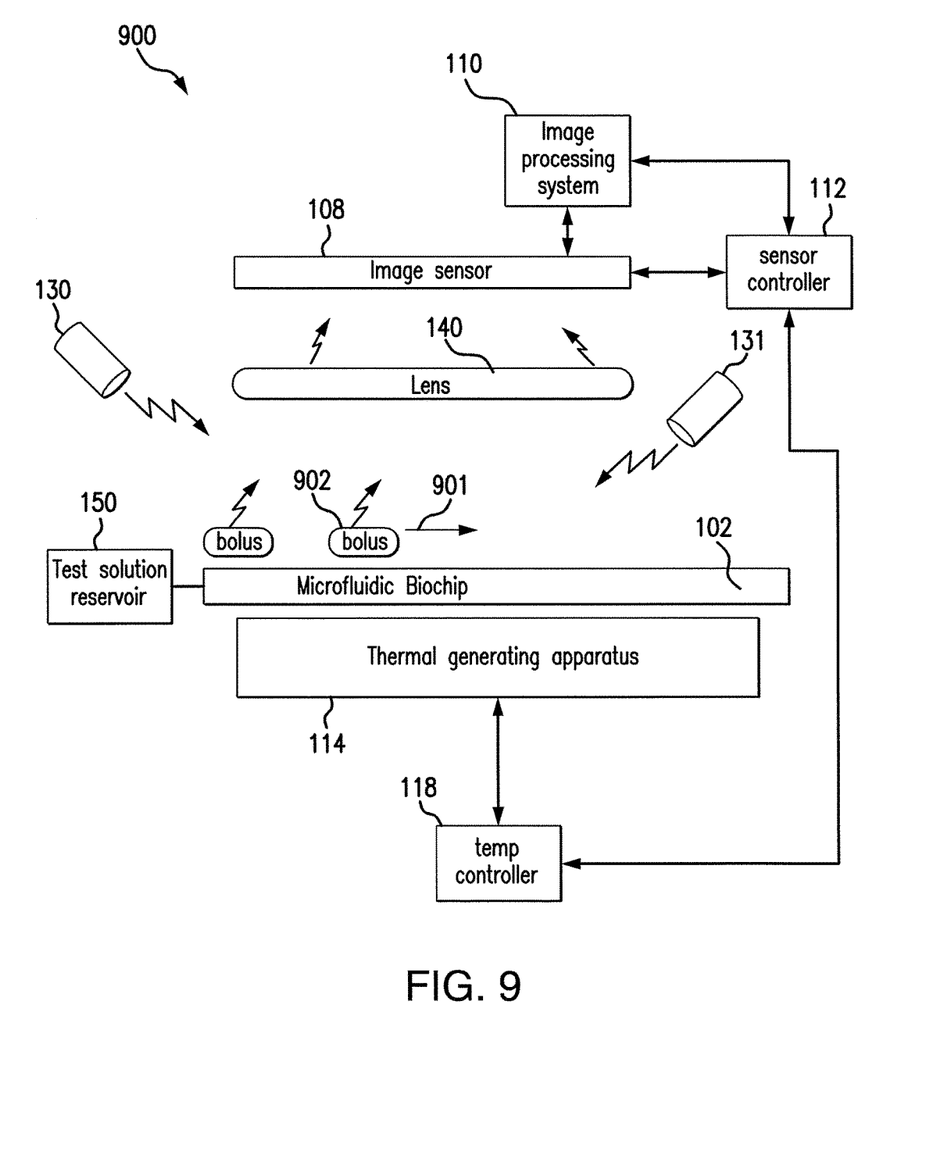
FIG. 9 is a functional block diagram of a nucleic acid analysis system according to one embodiment.

Referring now to FIG. 9, FIG. 9 is a functional block diagram illustrating a nucleic acid analysis system 900 according to another embodiment of the invention.

As illustrated in FIG. 9, system 900 may include many of the same components as system 100. For example, system 900 includes a substrate 102 having at least one microfluidic channel; at least one thermal generating unit 114, which is operable to provide heat to and/or absorb heat from at least a portion of the microfluidic channel, such as, for example, a thermal generating unit disclosed in U.S. patent application Ser. No. 11/505,358, incorporated herein by reference. The system 900 may also include a temperature controller 118 for controlling apparatus 114; an image sensor 108 disposed in relation to the substrate such that at least a portion of the microfluidic channel is within the field of view of image sensor 108; an image sensor controller 110; and an image processing system 112 coupled to image sensor 108.

Like system 100, system 900 may be used to analyze a sample of nucleic acid (e.g., bolus 902). More specifically, system 900 may be used to amplify DNA and then melt the amplified DNA. In one embodiment, to amplify the DNA, a sample of a solution containing real-time PCR reagents may be introduced into the microfluidic channel and then forced to move through the channel in the direction of arrow 901 using techniques well known in the art.

While the sample is moving through the channel, temperature controller 118 may be configured to cause thermal generating apparatus 114 to cycle the temperature of the sample as described above. For example, in response to receiving a predetermined input, temperature controller 118 may cause thermal generating apparatus 114 to cycle the temperature of the sample.

While the sample is undergoing amplification, image sensor controller 110 may cause the image sensor to capture images of a segment of the channel in which the sample is located, thereby capturing image data corresponding to emissions from the sample. In some embodiments, image sensor controller may cause image sensor 108 to capture at least one image each cycle and, to improve throughput, may window the image sensor to read out only a predetermined subset of the sensor's pixel array.

Image processing system 112 may be configured to receive this image data from image sensor 108 and use the image data to determine whether the intensity of emissions from the sample equals or exceeds a predetermined emission intensity threshold. Additionally or alternatively, image processing system 112 may be configured to use the image data to determine the rate of change in the intensity of emissions from the sample.

Further, temperature controller 118 may be configured to cause thermal generating apparatus 114 to gradually ramp the temperature of the sample from a first temperature (e.g., about 65 degrees Celsius) to a second temperature (e.g., about 95 degrees Celsius) in response to the occurrence of a particular event.

For example, temperature controller 118 may be configured to cause thermal generating apparatus 114 to gradually ramp the temperature of the sample from the first temperature to the second temperature in response to image processing system 112 determining that (a) the intensity of emissions from the sample equals or exceeds a predetermined emission intensity threshold or (b) the rate of change in the intensity of emissions from the sample is less than or equal to a predetermined threshold. In other embodiments, temperature controller 118 may be configured to cause thermal generating apparatus 114 to gradually ramp the temperature of the sample from the first temperature to the second temperature in response to: a determination that (a) the sample has been exposed to at least a certain number of temperature cycles, (b) a predetermined amount of time has elapsed from a specific earlier point in time (e.g., the point in time when the sample entered the PCR processing zone 104 or the point in time when the sample was exposed to its first temperature cycle), or (c) the sample is within a predefined region of the channel (e.g., within HRTm zone 106).

In some embodiments, in response to the particular event, temperature controller 118 may cause thermal generating apparatus 114 to ramp the temperature by increasing the amount of provided heat at a thermal ramp rate of between about 0.1 to 2 degree Celsius (C) per second.

While the temperature of the sample is being ramped, image sensor controller 110 may cause image sensor 108 to capture images of the segment of the channel in which the sample is located, thereby capturing image data corresponding to emissions from the sample. More specifically, in some embodiments, image sensor controller 110 causes image sensor 108 to capture at least 5 images per second of the segment of the channel in which the sample is located (and preferably 10 images or more per second).

In some embodiments, in response to image processing system 112 determining that the intensity of emissions from the sample equals or exceeds the predetermined emission intensity threshold, excitation source 131 is employed to illuminate the segment of the channel in which the sample is located, thereby illuminating the sample while the sample undergoes thermal melting.

Figure 10:
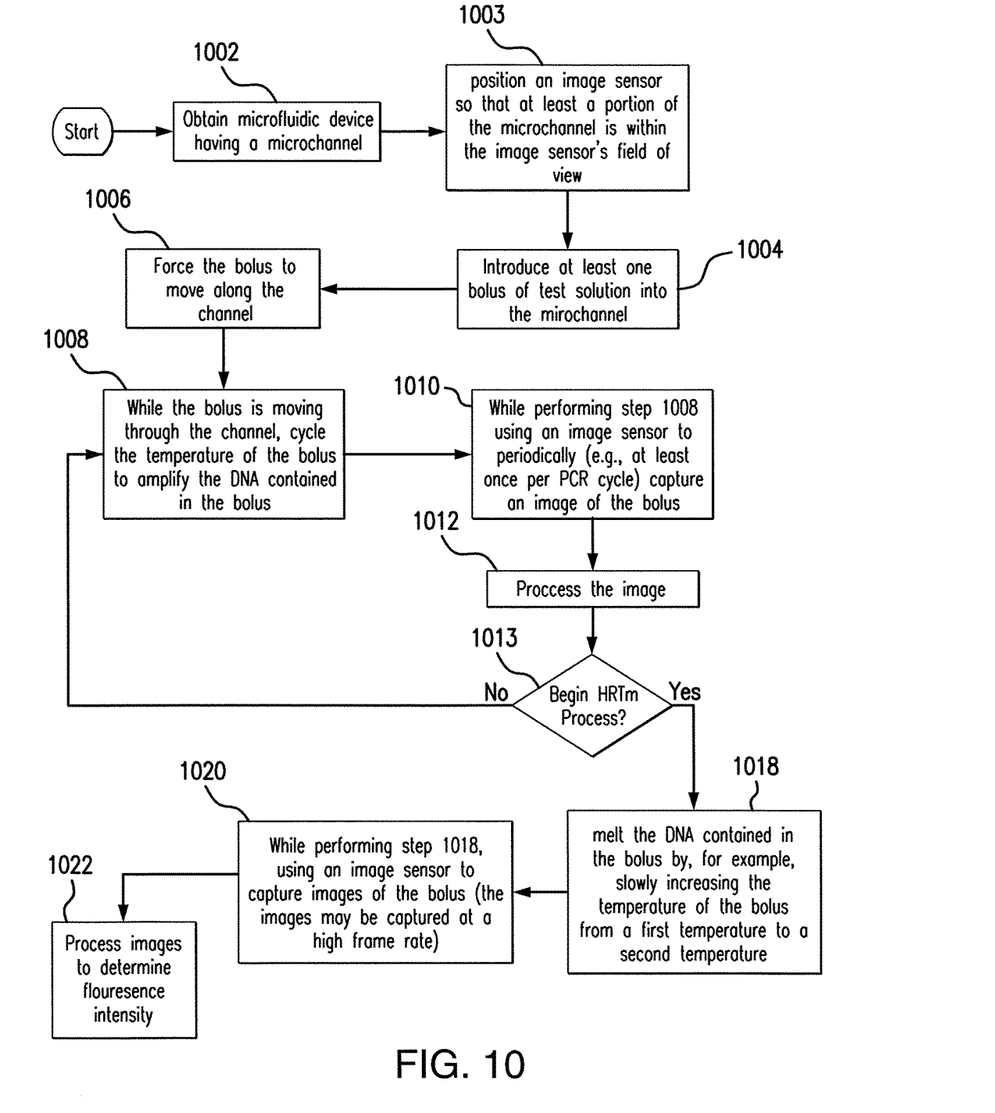
FIG. 10 is a flow chart illustrating a process according to an embodiment.

Referring now to FIG. 10, FIG. 10 is a flow chart illustrating at least some of the steps of the process described above. The process shown in FIG. 10 may start in step 1002 where a device having a microfluidic channel is obtained. In step 1003, an image sensor is positioned so that at least a portion of the channel is within the image sensor's field of view. In step 1004, a sample of solution is introduced into the channel. In step 1006, the sample is forced to move along the channel. In step 1008, while the sample is moving through the channel, the temperature of the sample is cycled to amplify DNA contained in the sample.

In step 1010, while step 1008 is being performed, the image sensor is used to produce image data corresponding to emissions from the sample. In step 1012, the image data is processed (e.g., the image data may be processed to determine the intensity of the emissions). In step 1013, a determination is made as to whether the DNA melting process (e.g., HRTm) should be initiated. If not, the process may return to step 1008, otherwise it may proceed to step 1018.

As described above, there are several ways this determination can be made. For example, in one embodiment, a processor (e.g., a processor of temperature controller 118)

keeps track of the number of temperature cycles the sample has been exposed to and if the number meets or exceeds a threshold, then the melting process should be initiated (i.e., the process should proceed to step 1018). In another embodiment, if it is determined that the emission intensity from the sample is greater than or equal to a predetermined threshold, then the process should proceed to step 1018. In yet another embodiment, the step of determining whether to begin the melting process includes examining the rate of change of the emission intensity from the sample and initiating the melting process if the rate of change is less than or equal to a predetermined threshold. In still another embodiment, the step of determining whether to begin the melting process includes determining whether (i) a predetermined amount of time has elapsed from a specific earlier point in time (e.g., the point in time when the sample entered the PCR processing zone 104 or the point in time when the sample was exposed to its first temperature cycle) or (ii) the sample is within a predefined region of the channel (e.g., within HRTm zone 106).

In step 1018, heat may be provided or removed from the sample so that the sample reaches a predetermined temperature (e.g., about 65 degrees Celsius) and then heat is provided to the sample to melt DNA within the sample. As described above, the heat may be provided so that the temperature of the sample increases substantially at a constant rate to a predetermined temperature (e.g., at least about 95 degrees Celsius). In step 1020, while step 1018 is being performed, an image sensor is used to produce image data corresponding to emissions from the sample. Preferably, in step 1020 the images are captured at a higher frame rate than the images captured in step 1010 (for example, in step 1020 the image sensor may be configured to capture at least 5, and preferably about 10, images per second). To achieve the higher frame rate, the image sensor may be windowed such that fewer than all of the pixels of the sensor's pixel array are readout. In step 1022, the image data collected in step 1020 may be processed.

Figure 11:
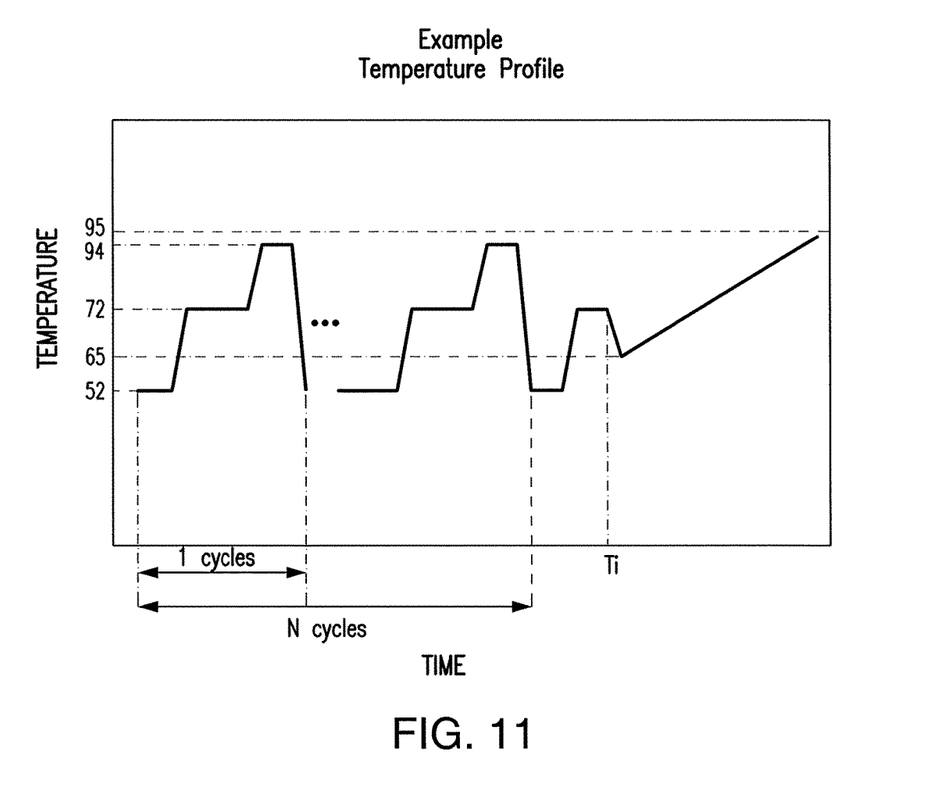
FIG. 11 is an example temperature profile.

Referring now to FIG. 11, FIG. 11 illustrates the temperature profile of a sample that undergoes the processing described above. As shown in FIG. 11, the temperature of the sample is cycled for a period of time so that the sample is exposed to some number of temperature cycles. In the illustrated example, at time t=Ti, the image processing system determines that (a) the intensity of the emissions from the sample meets or exceeds a threshold or (b) the rate of change of the intensity of the emissions from the sample is less than or equal to a threshold, either of which may be an indication that the DNA in the sample has been sufficiently amplified. Accordingly, as shown in FIG. 11, at about time t=Ti, the temperature of the sample is brought to about 65 degrees Celsius and then the temperature of the sample increases at substantially a constant rate so that the temperature reaches a predetermined temperature (e.g., about 95 degrees Celsius).

While various embodiments of the present invention have been described above, it should be understood that they have been presented by way of example only, and not limitation. Thus, the breadth and scope of the present invention should not be limited by any of the above-described exemplary embodiments.

Additionally, while the processes described above are shown as a sequence of steps, this was done solely for the sake of illustration. Accordingly, it is contemplated that some steps may be added, some steps may be omitted, and the order of the steps may be re-arranged.

For the claims below the words "a" and "an" should be construed as "one or more."

What is claimed is:

1. A method, comprising:
   (a) introducing into a microchannel at least one bolus containing nucleic acid;
   (b) forcing the bolus to move through the microchannel;
   (c) while the bolus is moving through the microchannel,
      (i) causing a thermal generating apparatus to cycle the temperature of the bolus to amplify nucleic acid contained in the bolus, wherein the thermal generating apparatus sequentially controls temperature during amplification and thermal denaturation, the thermal denaturation being performed after the amplification is completed and (ii) at least once per temperature cycle determining whether a predetermined emission intensity threshold has been met, wherein the step of determining whether the predetermined emission intensity threshold has been met comprises using an image sensor to capture an image of the bolus and processing the captured image data to determine the intensity of light emitted from the bolus;
   (d) in response to determining that the predetermined emission intensity threshold has not been met, then repeating step (c); and
   (e) in response to determining that the predetermined emission intensity threshold has been met, then, causing said thermal generating apparatus to cease the temperature cycling and causing said thermal generating apparatus to gradually increase the temperature of the bolus, while the bolus is still moving through the microchannel, causing thermal denaturation of dsDNA within the bolus to transition to ssDNA and using the image sensor to capture images of the bolus.

2. The method of claim 1, wherein the step of determining whether the predetermined emission intensity threshold has been met further comprises (a) comparing a value representing the determined intensity to a threshold value or (b) determining the rate of change in the intensity of the emissions from the bolus.

3. The method of claim 2, further comprising initiating a process for causing the dsDNA within the bolus to transition to ssDNA in response to determining that the result of the comparison indicates that the value representing the determined intensity is greater than the threshold value.

4. The method of claim 1, wherein the temperature is increased at or about a constant rate.

5. The method of claim 4, wherein the constant rate is between about 0.1 and 2 degree Celsius per second.

6. The method of claim 1, wherein the step of using the image sensor to capture an image of the bolus comprises determining a region of interest within the field of view of the image sensor and then reading out only those pixels of the image sensor that correspond to the region of interest.

7. The method of claim 1, wherein step (c) further comprises
   (iii) determining whether (a) the bolus has been exposed to at least a predetermined number of PCR temperature cycles, (b) at least a predetermined amount of time has elapsed since particular point in time, and/or (c) the bolus has entered a predefined region of the microchannel.

8. A method for use in a system comprising a substrate comprising a channel, the method comprising:
   forcing a sample of a solution containing real-time PCR reagents to move though the channel; and while the sample is moving through an analysis region of the channel performing the steps of:

(a) causing thermal generating apparatus to cycle the temperature of the sample, wherein the thermal generating apparatus sequentially controls temperature during amplification and thermal denaturation, the thermal denaturation being performed after the amplification is completed;

(b) at least once per temperature cycle, determining whether nucleic acid in the sample has been sufficiently amplified by using an image sensor to capture an image of the bolus and processing the captured image data to determine the intensity of light emitted from the bolus;

(c) in response to determining that a rate of change in the intensity of light emitted from the bolus is less than a predetermined threshold, causing said thermal generating apparatus to cease the cycling of the temperature of the sample and causing said thermal generating apparatus to gradually increase the sample's temperature from a first temperature to a second temperature to cause thermal denaturation of the nucleic acid; and (d) while the step of gradually increasing the sample's temperature is performed, using an image sensor to monitor emissions from the sample.

9. The method of claim 8, wherein the step of determining whether the nucleic acid in the sample has been sufficiently amplified comprises determining the intensity of light emitted from the sample and comparing the determined intensity to an intensity threshold value.

10. The method of claim 9, wherein the step of using the image sensor to capture an image of the sample comprises determining a region of interest within the field of view of the image sensor and then reading out only those pixels of the image sensor that correspond to the region of interest.

11. The method of claim 8, wherein the step of cycling the temperature of the sample comprises performing the following steps one or more times: (i) holding the temperature of the sample at or about a first temperature for at least a first period of time; (ii) after step (i), using the thermal generating apparatus to heat the temperature of the sample from the first temperature to a second temperature; (iii) after step (ii), holding the temperature of the sample at or about the second temperature for at least a second period of time; (iv) after step (iii), using the thermal generating apparatus to heat the temperature of the sample from the second temperature to a third temperature; (v) after step (iv); holding the temperature of the sample at or about the third temperature for at least a third period of time.

12. The method of claim 8, wherein the step of gradually increasing the temperature of the sample from the first temperature to the second temperature comprises increasing the temperature at or about a constant rate.

13. The method of claim 12, wherein the constant rate is between about 0.1 and 1 degrees Celsius per second.

14. The method of claim 13, wherein increasing the temperature at or about a constant rate comprises increasing the temperature at said rate for at least about 1 minute.

15. The method of claim 8, further comprising the step of keeping a record of the number of temperature cycles to which the sample is exposed.

16. The method of claim 15, further comprising the step of determining whether the sample has been exposed to at least a predetermined number of temperature cycles.

17. The method of claim 8, further comprising the step of determining whether at least a predetermined amount of time has elapsed since a particular point in time.

18. The method of claim 8, further comprising the step of determining whether the sample has entered a predefined region of the channel.

19. A method, comprising:

(a) introducing into a microchannel at least one bolus containing nucleic acid;

(b) forcing the bolus to move through the microchannel;

(c) while the bolus is moving through the microchannel,
(i) controlling a thermal generating apparatus to cycle the temperature of the bolus to amplify nucleic add contained in the bolus, wherein the thermal generating apparatus sequentially controls temperature amplification and thermal denaturation, the thermal denaturation being performed after the amplification is completed and (ii) determining at least once per temperature cycle whether the bolus has been exposed to at least a predetermined number of temperature cycles; and (d) in response to determining that the bolus has been exposed to at least a predetermined number of temperature cycles, then, ceasing the temperature cycling and, while the bolus is still moving through the microchannel, controlling said thermal generating apparatus to cause thermal denaturation of dsDNA within the bolus to transition to ssDNA and using an image sensor to capture images of the bolus.

20. The method of claim 19, wherein the step of determining whether the bolus has been exposed to at least a predetermined number of temperature cycles comprises using the image sensor to capture an image of the bolus.

21. The method of claim 20, wherein the step of determining whether the bolus has been exposed to at least a predetermined number of temperature cycles further comprises processing the captured image data to determine the intensity of light emitted from the bolus.

22. The method of claim 21, wherein the step of determining whether the bolus has been exposed to at least a predetermined number of temperature cycles further comprises (a) comparing a value representing the determined intensity to a threshold value or (b) determining the rate of change in the intensity of the emissions from the bolus.

23. The method of claim 22, further comprising initiating a process for causing the dsDNA within the bolus to transition to ssDNA in response to determining that the result of the comparison indicates that the value representing the determined intensity is greater than the threshold value.

24. The method of claim 23, wherein the step of initiating the process comprises configuring the thermal generating apparatus to gradually increase the temperature of the bolus.

25. The method of claim 20, wherein the step of determining whether the bolus has been exposed to at least a predetermined number of temperature cycles further comprises using the image sensor to capture an image of the bolus at least once during each temperature cycle.

* * * * *